US009155854B2

(12) United States Patent
Hayman et al.

(10) Patent No.: US 9,155,854 B2
(45) Date of Patent: Oct. 13, 2015

(54) TRACHEAL TUBE WITH VISUALIZATION DEVICE AND INTEGRATED FLUSHING SYSTEM

(75) Inventors: Sarah Hayman, Boulder, CO (US); Lockett Wood, Lyons, CO (US); Neville DeWitt Pierrat, Golden, CO (US)

(73) Assignee: Covidien LP, Mansfield, MA (US)

( * ) Notice: Subject to any disclaimer, the term of this patent is extended or adjusted under 35 U.S.C. 154(b) by 403 days.

(21) Appl. No.: 13/222,645

(22) Filed: Aug. 31, 2011

(65) Prior Publication Data

US 2013/0053636 A1  Feb. 28, 2013

(51) Int. Cl.
| A61B 1/04 | (2006.01) |
| A61B 1/00 | (2006.01) |
| A61M 16/04 | (2006.01) |
| A61B 1/015 | (2006.01) |
| A61B 1/05 | (2006.01) |

(52) U.S. Cl.
CPC ............ *A61M 16/04* (2013.01); *A61B 1/00082* (2013.01); *A61B 1/015* (2013.01); *A61B 1/05* (2013.01); *A61M 16/0404* (2014.02); *A61M 16/0434* (2013.01); *A61M 16/0459* (2014.02); *A61M 16/0477* (2014.02); *A61M 16/0463* (2013.01); *A61M 2205/0205* (2013.01); *A61M 2205/3306* (2013.01)

(58) Field of Classification Search
None
See application file for complete search history.

(56) References Cited

U.S. PATENT DOCUMENTS

| 4,685,457 A | 8/1987 | Donenfeld |
| 4,846,153 A | 7/1989 | Berci |
| 4,949,716 A | 8/1990 | Chenoweth |
| 4,982,729 A | 1/1991 | Wu |
| 5,016,614 A | 5/1991 | MacAllister |
| 5,038,766 A | 8/1991 | Parker |
| 5,174,283 A | 12/1992 | Parker |
| 5,203,320 A | 4/1993 | Augustine |
| 5,259,377 A | 11/1993 | Schroeder |
| 5,285,778 A | 2/1994 | Mackin |
| 5,329,940 A | 7/1994 | Adair |
| 5,339,805 A | 8/1994 | Parker |
| 5,363,838 A | 11/1994 | George |
| 5,400,771 A | 3/1995 | Pirak et al. |
| 5,518,502 A * | 5/1996 | Kaplan et al. ............. 600/157 |
| 5,607,386 A | 3/1997 | Flam |
| 5,636,625 A | 6/1997 | Miyagi et al. |
| 5,694,929 A | 12/1997 | Christopher |
| 5,913,816 A | 6/1999 | Sanders et al. |
| 5,921,917 A | 7/1999 | Barthel et al. |
| 5,964,217 A | 10/1999 | Christopher |

(Continued)

OTHER PUBLICATIONS

U.S. Appl. No. 12/981,296, filed Dec. 29, 2010, Sarah Hayman.

(Continued)

*Primary Examiner* — Anhtuan T Nguyen
*Assistant Examiner* — Alexandra Newton
(74) *Attorney, Agent, or Firm* — Fletcher Yoder PC

(57) ABSTRACT

The present disclosure describes systems and methods that utilize a multi-lumen tube with an integral visualization apparatus, such as a camera. The multi-lumen tracheal tube system may include a camera apparatus that is positioned to facilitate left or right bronchial intubation. In addition, the camera apparatus may be a unitary assembly that functions to hold and position the camera relative to the tube and provides an acceptable profile for comfortable intubation. The camera apparatus may include additional components, such as integral light sources and flushing or cleaning devices to remove any buildup from the camera or optical components.

20 Claims, 5 Drawing Sheets

(56) References Cited

U.S. PATENT DOCUMENTS

| | | | |
|---|---|---|---|
| 6,142,144 | A | 11/2000 | Pacey |
| 6,189,533 | B1 | 2/2001 | Simon et al. |
| 6,196,225 | B1 | 3/2001 | Allgeyer |
| 6,520,183 | B2 | 2/2003 | Amar |
| 6,543,446 | B1 | 4/2003 | Christopher |
| 6,568,388 | B2 | 5/2003 | Christopher |
| 6,629,924 | B2 | 10/2003 | Aydelotte |
| 6,631,713 | B1 | 10/2003 | Christopher |
| 6,672,305 | B2 | 1/2004 | Parker |
| 6,820,618 | B2 | 11/2004 | Banner et al. |
| 6,849,042 | B2 | 2/2005 | Christopher |
| 6,929,600 | B2 | 8/2005 | Hill |
| 7,052,456 | B2 | 5/2006 | Simon |
| 2006/0025650 | A1* | 2/2006 | Gavriely ............. 600/110 |
| 2006/0122460 | A1 | 6/2006 | Kamali |
| 2007/0137651 | A1 | 6/2007 | Glassenberg et al. |
| 2007/0260120 | A1* | 11/2007 | Otawara ............. 600/129 |
| 2008/0039715 | A1 | 2/2008 | Wilson et al. |
| 2008/0230070 | A1* | 9/2008 | Gregorian ............. 128/207.14 |
| 2010/0030057 | A1 | 2/2010 | Gavriely et al. |
| 2010/0113916 | A1* | 5/2010 | Kumar ............. 600/424 |
| 2010/0147311 | A1* | 6/2010 | Nierich ............. 128/207.14 |
| 2012/0024292 | A1 | 2/2012 | Sandmore et al. |
| 2012/0172664 | A1 | 7/2012 | Hayman et al. |
| 2012/0179009 | A1 | 7/2012 | Gavriely |
| 2012/0259173 | A1* | 10/2012 | Waldron et al. ............. 600/109 |
| 2012/0298111 | A1 | 11/2012 | Wood et al. |
| 2013/0158351 | A1* | 6/2013 | Daher et al. ............. 600/109 |

OTHER PUBLICATIONS

Salem, MR, "Verification of Endotracheal Tube Placement", Anesthesiology Clinics of North America, vol. 19(4); pp. 831-839 (Dec. 1, 2001).

Kristensen, MS, "The Parker Flex-Tip Tube versus a Standard Tube for Fiberoptic Orotracheal Intubation", Anesthesiology. vol. 98. No. 2. Feb. 2003.

Kohase, H. et al., "Endotracheal Intubation Device with a Charge Couple Device Camera", Anesth. Analg. 2003; 96:43-4.

Makin, H. et al., "The Effects of Traceal Tube Tip Design and Tube Thickness on Laryngeal Pass Ability During Oral Tube Exchange with an introducer", Anesth Analog 2003; 97:285-8.

Sehata, H. et al., "Tracheal intubation using a new CCD camera-equipped device: a report of two cases with a difficult intubation", Acta Anaesthesiologica Scandinavica, vol. 49, No. 8, Sep. 2005, pp. 1218-1220(3).

Kaplan, MB et al., "Seeing is believing: the importance of video laryngoscopy in teaching and in managing the difficult airway", Surg. Endosc. Apr. 2006;20 Suppl 2:S479-83. Epub Mar. 16, 2006.

Arndt Endobronchial Blocker, Cook Medical, http://www.cookmedical.com/cc/familyListingAction.do?family=Endobronchial+Blockers.

Cohen Endobronchial Blocker, Cook Medical, http://www.cookmedical.com/cc/familyListingAction.do?family=Endobronchial+Blockers.

Portex, Endobronchial Double Lumen, Smiths-Medical, http://www.smiths-medical.com/catalog/endotracheal-tubes.

Respiratory Care—http://www.smiths-medical.com/markets/respiratory-care/ (Apr. 1, 2010).

* cited by examiner

TRACHEAL TUBE WITH VISUALIZATION DEVICE AND INTEGRATED FLUSHING SYSTEM

BACKGROUND

The present disclosure relates generally to medical devices and, more particularly, to multi-lumen tracheal tubes that may accommodate a visualization device, such as a camera, and that include mechanisms for cleaning the camera during use.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tracheal tube (e.g. endotracheal, endobronchial, nasotracheal, or transtracheal device) may be used to control the flow of gases into the trachea of a patient. Often, a seal between the outside of the tube and the interior wall of the tracheal lumen is required, allowing for generation of positive intrathoracic pressure distal to the seal and prevention of ingress of solid or liquid matter into the lungs from proximal to the seal.

Depending on the clinical condition of the patient, a tracheal tube may be inserted that is capable of ventilating one lung to the exclusion or independently of the other. For example, during thoracic surgery, surgeons may wish to isolate and perform surgery on an affected lung while simultaneously ventilating the healthy lung in order to optimize the surgical field and/or avoid cross-contamination.

Endobronchial tubes that allow independent control of each lung through dual lumens are typically used for this purpose. One lumen is opened to ambient pressure to isolate the desired lung, while respiratory and anesthetic gases are delivered via positive pressure ventilation through the other lumen. Placement of an endobronchial tube not only requires corroboration of correct insertion and positioning within the trachea, but also additional corroboration of correct insertion and positioning within the desired mainstem bronchus. Placement must be reassessed frequently after patient position changes for surgical indications (e.g. lateral decubitus positioning), during surgical manipulations and after tube manipulations. This corroboration of placement requires bronchoscopic evaluation through the tracheal and/or bronchial lumen to visualize whether the bronchial lumen has been correctly cannulated and whether the tip of the bronchial lumen is correctly positioned. However, bronchoscopy is time consuming, can interrupt ventilation, and requires additional skills on the part of the provider. In addition, bronchoscopes are bulky, expensive, prone to damage, and difficult to operate within the relatively small diameter of the bronchial lumen.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
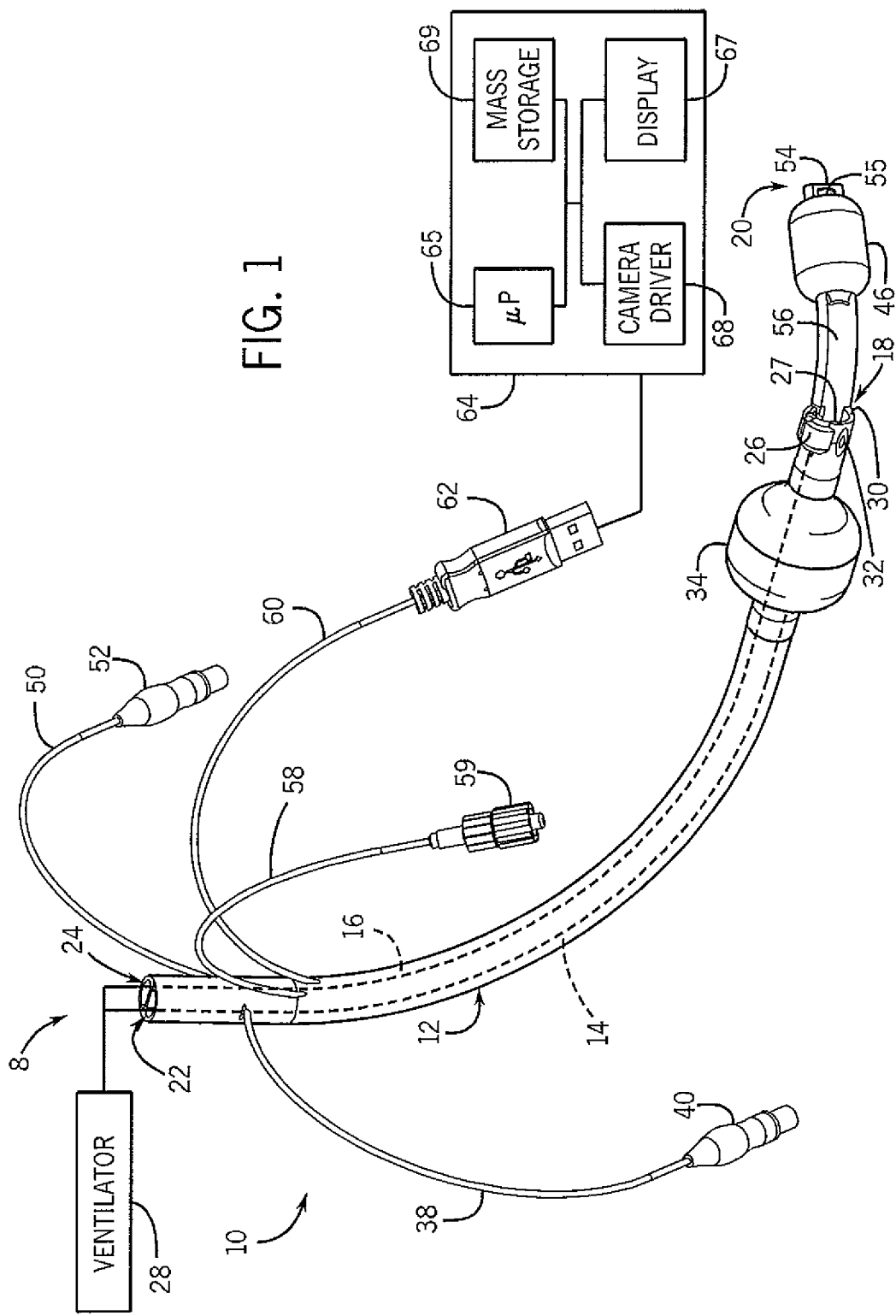
FIG. 1 is an elevational view of an endobronchial tube including a visualization device in accordance with aspects of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, embodiments of a tracheal tube having an integral visualization apparatus and flushing or cleaning system for removing debris from the visualization apparatus are provided herein. In a particular embodiment, the tracheal tube may be an endobronchial tube. Endobronchial tubes are double-lumen tracheal tubes that facilitate an airtight seal in the trachea and one stem of a patient bronchus to allow independent ventilation of one lung. Generally, an endobronchial tube includes two tubes of unequal length that are attached. One tube terminates within the tracheal airway space, i.e., the shorter tube has a distal end at a location similar to a typical endotracheal tube. The other, longer, tube is configured to extend past the shorter tube and into a left or right bronchial stem. Both tubes define a passageway for transferring fluids to and from a patient.

While the total diameter of an endobronchial tube may be larger than that of a single lumen endotracheal tube, the diameter of each individual lumen of the endobronchial tube is relatively smaller than that of a single lumen endotracheal tube. Such a shift in diameter may be challenging for physicians during placement of an endobronchial tube. Because the endobronchial tube involves not only correct intubation within the trachea but also correct placement of the bronchial lumen with a left or right bronchial stem, physicians may use visualizing devices such as bronchoscopes to aid in the placement of the bronchial tube. However, commercial bronchoscopes are generally sized and shaped to be used in conjunction with the relatively larger lumen of a single-lumen endotracheal tube. As such, the bronchoscopes may not fit easily within either lumen of a double-lumen endobronchial tube.

The tracheal tubes provided herein include built-in visualization devices that may offer several useful functionalities, such as facilitating proper placement of the tube through the vocal cords, into the trachea; facilitating subsequent proper placement into the appropriate mainstem bronchus; facilitating intermittent or continuous corroboration of positioning within the mainstem bronchus via visual assessment; and/or facilitating intermittent or continuous evaluation of a patient's medical condition via assessment of changes within the mainstem bronchus or trachea (e.g. hemorrhage, accumulation of secretions, lung volume expansion, etc). These devices may preferably accomplish these endpoints with minimum to no impact on inner diameter of the tube lumens, no significant change in resistance to gas flow through the tube lumens, no interruption or reduction of fresh gas ventilation, and no requirement for use of a bronchoscope to assess tube placement or position. In addition, because endobronchial tubes are specifically designed for the anatomy of the right or left-mainstem bronchus, the built-in visualization devices are tailored to address specific challenges presented by the unique anatomic differences (e.g. right upper lobe occlusion). Further, the visualization techniques provided may include integral cleaning or flushing mechanisms that clear any accumulated fluid or debris from the surface of the camera. For example, during intubation, integral visualization devices may become obscured when relatively viscous fluids adhere to the camera surface or to its accompanying light sources. By delivering fluid or air through a flushing lumen on the tracheal tube, the camera and/or light source portion of the visualization device may be periodically cleaned.

The tracheal tubes as provided herein are preferably disposable rather than reusable, capable of providing differential mechanical ventilation to either or both lungs, and capable of supporting all other functions of standard endotracheal tubes (e.g. sealing, positive pressure generation, suctioning, irrigation, drug instillation, etc). The tracheal tubes may further be used in conjunction with acceptable auxiliary airway devices such as (e.g. heat and humidity conservers, thermometers, mechanical ventilators, humidifiers, closed suction systems, scavengers, capnometers, oxygen analyzers, mass spectrometers, PEEP/CPAP devices, etc). Furthermore, although the embodiments of the present disclosure illustrated and described herein are discussed in the context of tracheal tubes such as endobronchial tubes, it should be noted that presently contemplated embodiments may include a visualization device associated with any of a variety of suitable airway devices. For example, a visualization device as provided herein may be associated with a single-lumen tube, tracheostomy tube, a Broncho-Cath™ tube, a specialty tube, or any other airway device with a main ventilation lumen. Indeed, any device with a ventilation lumen designed for use in an airway of a patient may include a visualization device (e.g., a camera disposed on or within a collar). Furthermore, as used herein, the term "tracheal tube" may include an endotracheal tube, a tracheostomy tube, a double-lumen tube, a bronchoblocking tube, a specialty tube, or any other suitable airway device.

Turning now to the drawings, FIG. 1 is a perspective view of a system 8 including an exemplary tracheal tube 10 configured to be placed in a patient bronchial stem in accordance with aspects of the present disclosure. The tracheal tube 10 includes a central tubular body 12 with a tracheal ventilation lumen 14 and a bronchial ventilation lumen 16. The tracheal lumen terminates at a tracheal lumen distal end 18 while the bronchial lumen terminates in a bronchial lumen distal end 20. Furthermore, the tracheal tube 10 may include a tracheal lumen proximal end 22 and a bronchial lumen proximal end 24. As shown, the tracheal ventilation lumen 14 and a bronchial ventilation lumen 16 may be attached to one another over a portion of the tubular body 12 and may separate at their respective proximal ends 22, 24 and distal ends 18, 20. The tube 10 may include a visualization device 26 associated with one or both of the tracheal ventilation lumen 14 and the bronchial ventilation lumen 16. Over the portion of the tubular body 12 in which the tracheal ventilation lumen 14 and a bronchial ventilation lumen 16 are attached, the tubular body 12 may include a separating wall 27 (e.g., divider).

The tracheal lumen proximal end 22 and a bronchial lumen proximal end 24 may be outfitted with separate connectors that may be attached to a ventilation device 28 during operation that may include a suitable controller (e.g., a processor-based control system) so that a clinician may direct airflow to and from both the tracheal ventilation lumen 14 and bronchial ventilation lumen 16. In other embodiments, either tracheal ventilation lumen 14 or the bronchial ventilation lumen 16 may be blocked or otherwise closed such that only one of the two lumens of the tracheal tube 10 is operational.

The tracheal lumen distal end 18 of ventilation lumen 14 terminates in an opening 30 and may be placed in a patient trachea during operation to maintain airflow to and from the patient's lungs. A Murphy's eye 32 may be optionally present and located on the ventilation lumen 14 opposite the opening 30 to prevent airway occlusion when the tracheal tube assembly 10 is improperly placed within the patient's trachea. As illustrated, a tracheal cuff 34 may encircle the tubular body 12 and be inflated to seal against the walls of a body cavity (e.g., a trachea). The cuff 34 may be inflated via an inflation lumen terminating in an inflation tube 38 connected to an inflation pilot balloon and valve assembly 40. Additionally, it should be noted that the cuff 34 may be any suitable cuff, such as a tapered cuff, a non-tapered cuff, and so forth. The tracheal ventilation lumen 14 may also include a suction lumen (not shown) that extends from a location on the tracheal tube 10 positioned outside the body when in use to a location on the tubular body 12 that terminates in a port located proximally to cuff 34 through which secretions may be aspirated. Bronchial ventilation lumen 16 is longer than tracheal ventilation lumen 14 and includes a distal end 20 that extends past the tracheal lumen distal end 18. The bronchial ventilation lumen 16 may include a bronchial inflation cuff 46 that is configured to seal against the walls of a patient's bronchus. The cuff 46 may be inflated via an inflation lumen terminating in an inflation tube 50 connected to an inflation pilot balloon and valve assembly 52.

The tubular body 12 and the cuffs 34 and 46 may be formed from materials having desirable mechanical properties (e.g., puncture resistance, pin hole resistance, tensile strength, and so forth) and desirable chemical properties (e.g., biocompatibility). Further, in one embodiment, the walls of the cuff 34 or cuff 46 may be made of a polyurethane (e.g., Dow Pellethane® 2363-80A) having suitable mechanical and chemical properties. In other embodiments, the walls of the cuff 34 or cuff 46 may be made of silicone or a suitable polyvinyl chloride (PVC). In certain embodiments, the cuff 34 or cuff 46 may be generally sized and shaped as a high volume, low pressure cuff that may be designed to be inflated to pressures between about 15 cm $H_2O$ and 30 cm $H_2O$. Further, bronchial cuff 46 may be a different color or include other identifying markings that allow a user to differentiate between the tracheal cuff 34 and the bronchial cuff 46. In addition, to assist in proper placement of the tube 10, x-ray visible markings 56 may be placed at any appropriate location. For example, the markings 56 may outline a bronchial distal opening 54 or a side eye 55.

In addition, portions of the visualization device 26 may be formed from the same material or different materials as the tube 10. Generally, the visualization device 26 may be formed from biocompatible polymers and other nonreactive materials. It should also be understood that certain portions of the visualization device may be coated with antimicrobial materials to prevent bacterial adhesion or fouling. In embodiments in which camera lenses are coated, the antimicrobial coatings may be selected to minimize interference with image acquisition. The visualization device 26 may be adhered to or fastened to the tubular body 12 by any suitable process. For example, the visualization device 26 may be embedded in or adhered (e.g., welded) to tubular body 12. In addition, coupling to the tube 10 may be assisted by threading cables or other attachments into lumens formed in the tubular body 12. In particular embodiments, the tubular body 12 may include notches or recesses within the walls that accommodate the visualization device 26 and that do not impact the inner diameter of the ventilation lumens. Insofar as these recesses may be structurally less rigid than the rest of the tubular body 12, application of the visualization device 26 may restore rigidity to the relatively thinner recesses.

In one embodiment, the tube 10 may also include a fluid delivery lumen 58 in communication with the visualization device 26. The fluid delivery lumen 58 may terminate in a proximal coupler 59 that is sized and shaped to connect to a fluid source (e.g., a saline reservoir, a syringe). A portion of the fluid delivery lumen 58 may be formed within a wall of the tube 10. The fluid delivery lumen 58 may be configured to flush or clear mucus buildup on the visualization device 26. The tube 10 may also include a cable 60 coupled to the visualization device 26. The cable 60 may run along or within (e.g., in a dedicated lumen) the tubular body 12. The cable 60 may terminate in an electrical connector 62. In particular embodiments, the fluid delivery lumen 58 may deliver an appropriate fluid (e.g. saline) or air to an obscured surface of the visualization device 26. In particular embodiments, the delivery may be manual or may be controlled, e.g., via a device including a fluid source and processor-based controller for delivering fluid.

The system may also include a monitor 64 that may be configured to implement embodiments of the present disclosure and may be coupled to the visualization device 26 via connector 62 (e.g., a USB connector) and cable 60. It should be understood that the monitor 64 may be a stand-alone device or may, in embodiments, be integrated into a single device with, for example, the ventilator 28. The monitor 64 may include processing circuitry, such as a microprocessor 65 coupled to an internal bus and a display 67. In an embodiment, the monitor 64 may be configured to communicate with the tube via connector 62, to obtain signals from the visualization device 26. The information may then be stored in mass storage device 69, such as RAM, PROM, optical storage devices, flash memory devices, hardware storage devices, magnetic storage devices, or any suitable computer-readable storage medium. The information may be accessed and operated upon according to microprocessor 65 instructions. The monitor 64 may be configured to provide indications of tube placement within the trachea, such as an audio, visual or other indication, or may be configured to communicate the information to another device, such as the ventilator 28. In certain embodiments, the monitor 64 may also provide camera drive signals (including a drive signal to any associated light sources) to the visualization device 26 via camera driver 68. The drive signal from the camera driver 68 to the camera and light sources may be adjusted to reduce heating and power consumption of the visualization device 26. For example, the camera driver 68 may drive the camera continuously or intermittently or only at designated times during intubation. Further, the monitor 64 may also be configured to control deliver of fluid or air via the fluid delivery lumen 58.

Figure 2:
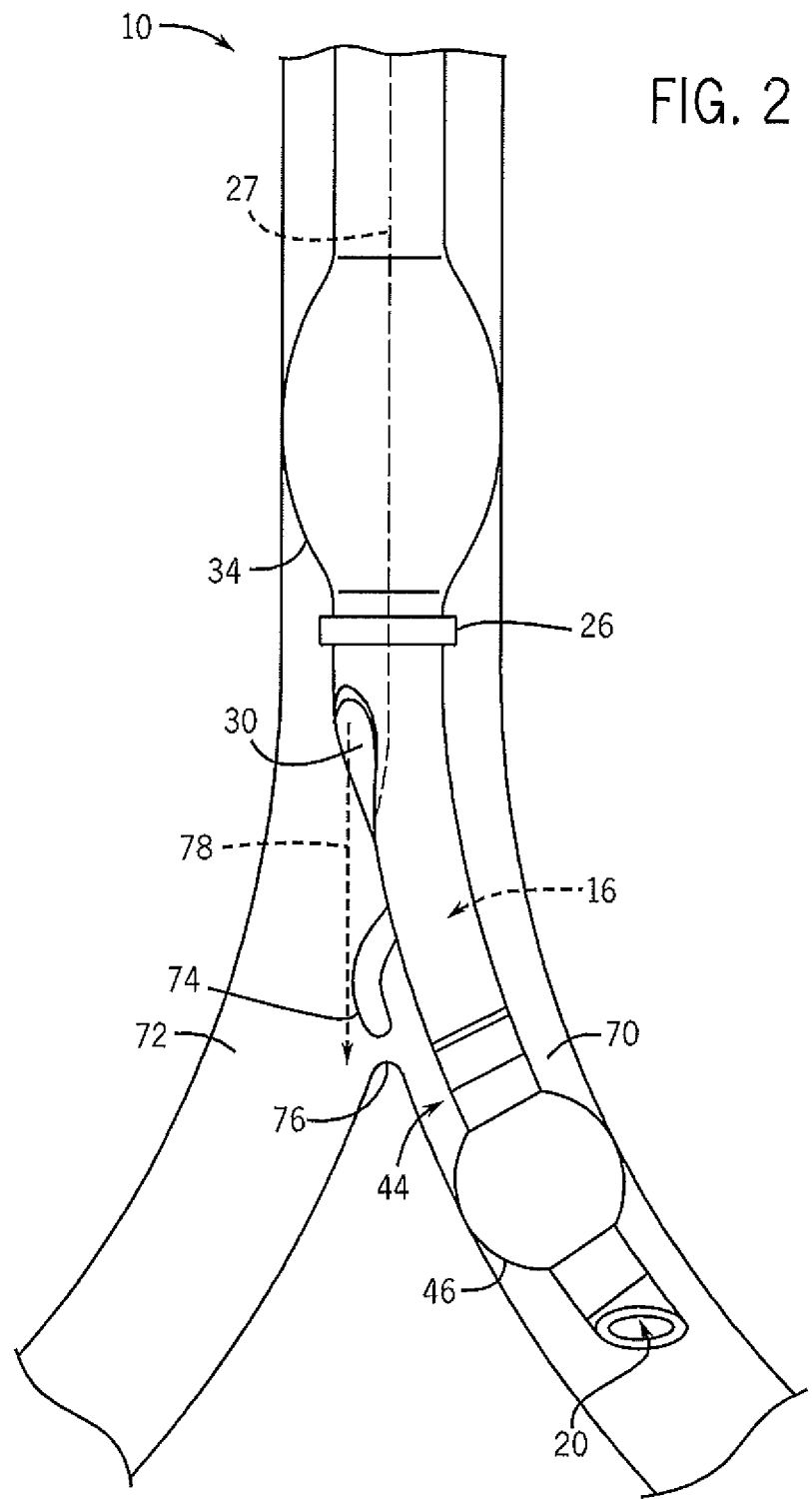
FIG. 2 is a perspective view of an exemplary endobronchial tube positioned within the left bronchus of a patient.

During operation, a tracheal tube 10 is inserted into the trachea of a patient and positioned within the left or right bronchial stem and the tracheal cuff 34 and bronchial cuff 46 are inflated to isolate the appropriate airway structures. In certain embodiments, a tracheal tube 10 may be configured to be positioned within a left bronchial stem 70, as shown in FIG. 2, In such an embodiment, the tube 10 may have particular features that assist in positioning the distal portion 44 and the bronchial cuff 46. For example, relative to the right bronchial stem 72, the left bronchial stein is relatively curved. Accordingly, the distal portion 44 may be curved in a similar manner. Further, the tube 10 optionally may include a protrusion 74 (e.g., carinal hook) to help position the tube 10 relative to the patient's carina 76.

After insertion of the tracheal tube 10, the visualization device 26 may be positioned so that its field of view is generally oriented in a distal direction (indicated by arrow 78). Such an orientation may allow viewing of the carina 76 or one or both of the left bronchial stem 70 or the right bronchial stem 72, which in turn may allow information about the placement of the tube 10 to be determined. In contrast to a bronchoscope, which is removed after the initial insertion of the tracheal tube 10, the visualization device 26 may be fixedly attached to the tracheal tube (e.g., via one or more of adhesion, heat welding, mechanical fasteners) so that information about tube placement may be collected throughout the intubation period. The visualization device 26 as depicted is associated with a distal region 18 of the tracheal ventilation lumen 14 such that the visualization device partially surrounds the lumen 14. In other embodiments, the visualization device may be located more distally on the tube 10. Further, additional visualization devices may be located on the tube 10 as appropriate. In other embodiments in which the visualization device 26 is associated with a single-lumen tube, the visualization device 26 may be located distal or on the distal shoulder of the cuff (e.g., in a distal region of a single-lumen tube).

Figure 3:
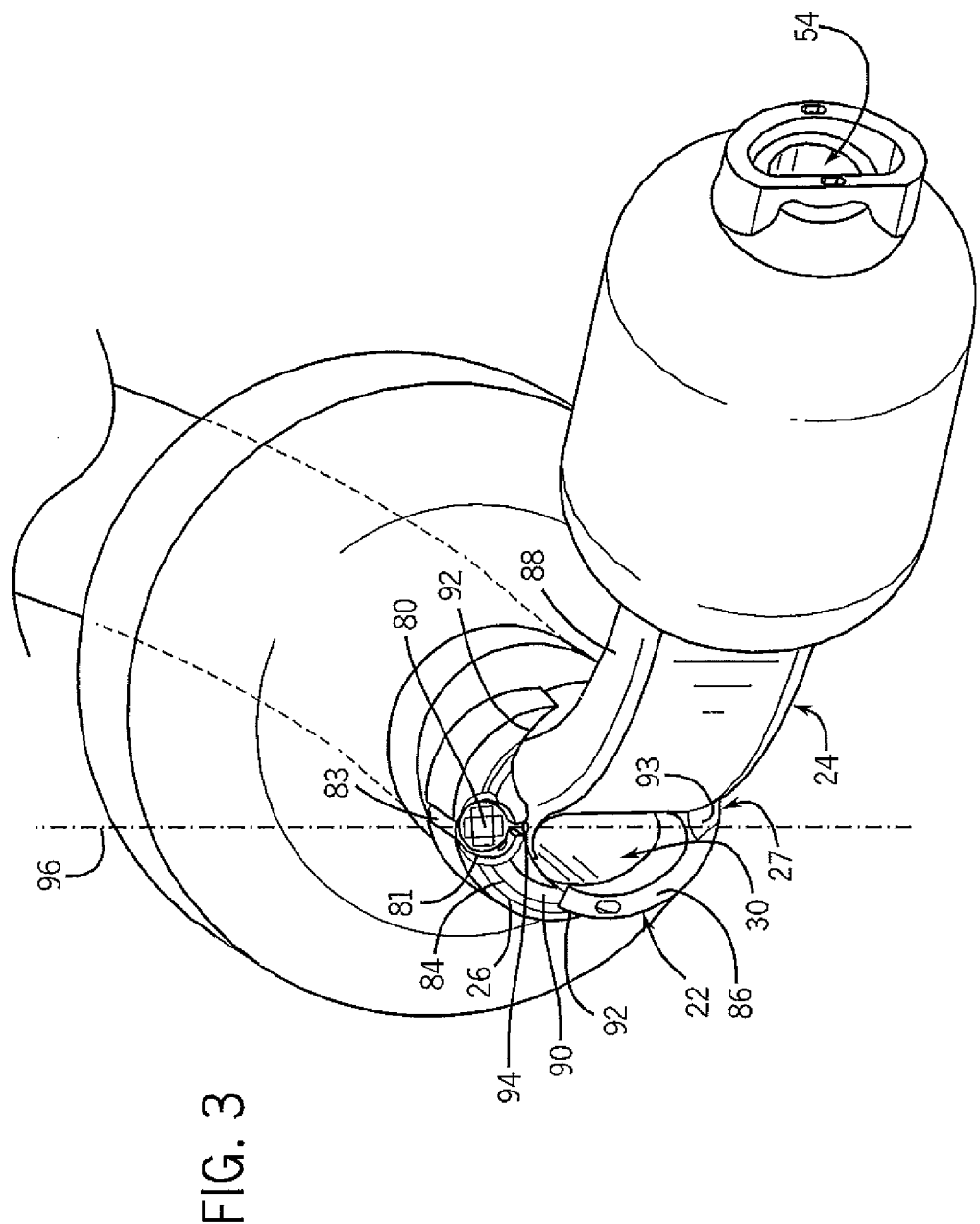
FIG. 3 is a bottom view of a visualization device associated with an endobronchial tube.

FIG. 3 illustrates a bottom view of an exemplary visualization device 26 associated with the tracheal tube 10. As shown, the visualization device 26 may include a camera 80 or other image gathering component that is suitably sized and shaped to be incorporated into the visualization device 26, e.g., a CMOS chip camera. Other suitable image gathering components may include pixel arrays or light guides coupled to an image gathering device. The camera 80 may be associated with one or more light sources 81 (e.g., light emitting diodes or fiber optic light sources). Supporting circuitry for the camera 80 and light sources 81 may be provided as part of a module or unit 83 that may be incorporated within the housing 84 of the visualization device. Connecting leads from the unit 83, including any light pipes for light sources 81, that extend to cable 60 may be positioned in dedicated lumens formed within the tubular body 12. Further, the supporting circuitry may be disposed on a circuit board, an electronic chip or incorporated on the camera chip itself.

As noted, the visualization device 26 may be affixed to the tubular body 12. In the depicted embodiment, a portion 90 of the housing 84 is embedded within a tracheal ventilation lumen wall 86 and a bronchial ventilation lumen wall 88. The embedded portion 90 is suitably sized and shaped to be embedded within or, in certain embodiments, form a portion of the tubular body 12. For example, the curvature of the housing 84 may be selected to match the curvature of one or both of the ventilations lumens 14 and 16. Extending wings 92 of the housing 84 may provide additional surface area for fixing the visualization device 26 to the tubular body 12.

The housing 84 may be any suitable size or shape to facilitate coupling to the tube 10. For example, the housing 84 may be an annulus, a partial annulus, a collar, or a saddle shape. The housing 84 and other portions of the visualization device 26 may be formed to reduce the profile that extends away from the tubular body 12 because it is desirable to limit the outer diameter of the tube 10, including any associated structures. In certain embodiments, the visualization device protrudes less than 5 mm, 4 mm, 3 mm, 2 mm, or 1 mm away from the tubular body 12, e.g., along axis 96 that is substantially orthogonal to the flow path of the tracheal ventilation lumen 14. In addition, the housing 84 may be formed so that more than 50% of the total volume of the visualization device 26 is embedded within or forms a portion of the tubular body 12. To that end, the supporting circuitry for image collection may be partially or completely disposed within the relatively thicker embedded portion 90. In particular embodiments, the visualization device 26 may be affixed to the tube 10 at certain portions of the tubular body 12 that are relatively thicker and may provide better support for the weight and volume of the visualization device 26. For example, the junction 93 of the separating wall 27, tracheal ventilation lumen wall 86, and the bronchial ventilation lumen wall 88 may be the thickest point along the tracheal tube 10. As such, the camera 80 of the visualization device 26 may be circumferentially aligned with junction 93. Such alignment may also facilitate improved image acquisition with regard to certain anatomical features, such as the carina 76. In particular embodiments, the camera 80 may be circumferentially aligned within 10 degrees, within 15 degrees, or within 30 degrees of junction 93.

In particular embodiments, it may be advantageous to align the camera 80 anterially. For example, the camera 80 may be positioned on the portion of the tubular body 12 that touches the anterior wall of the trachea when inserted. In particular, for a left-sided or a right-sided bronchial tube, anterior alignment may be advantageous In addition, it may be advantageous to affix the visualization device 26 on the bronchial ventilation lumen 16 below the tracheal lumen distal opening 30 but proximal to the carina 76. In the depicted embodiment, the housing 84 and camera 80 are aligned with the fluid delivery lumen 58 (see FIG. 1), which terminates at the distal end 94. Such alignment facilitates fluid delivery to the surface of the camera 80 and, in certain embodiments, the associated lights 81.

Figure 4:
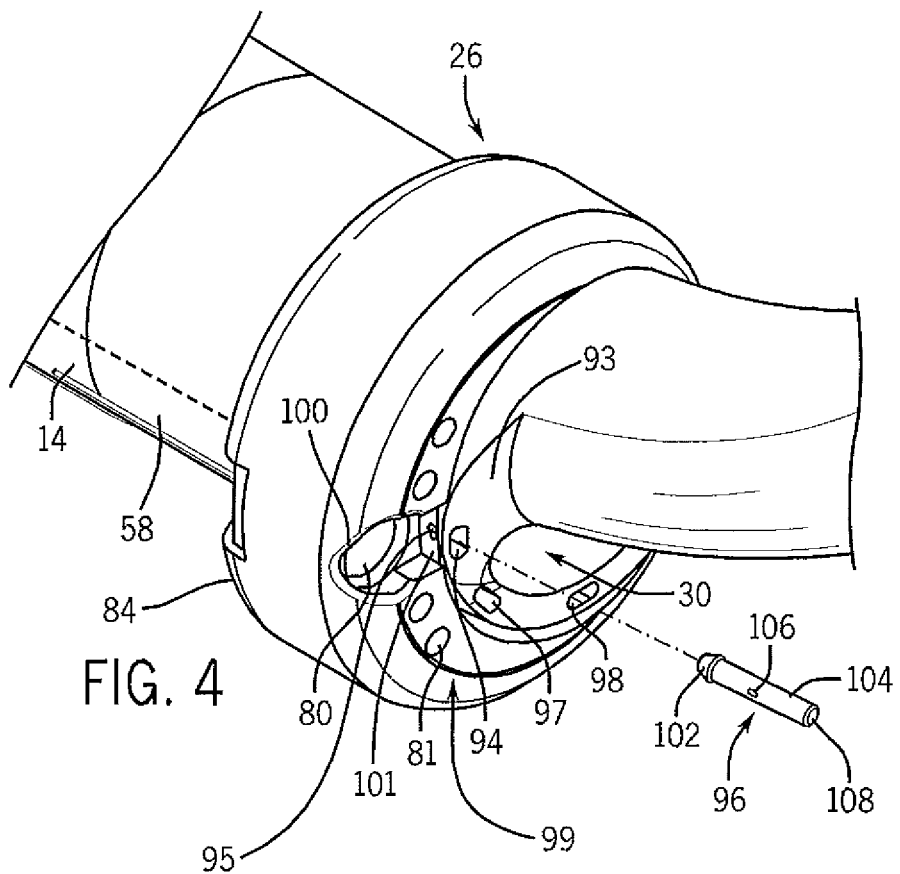
FIG. 4 is an exploded view of a visualization device and fluid nozzle component.

FIG. 4 is a perspective view of an exemplary visualization device 26 with an annular housing 84. In certain embodiments, the camera 80 may be aligned with the fluid delivery lumen 58. The fluid delivery lumen 58 (see FIG. 1) extends along the tubular body 12 and includes an opening 95 (e.g., a second opening) proximate to the visualization device 26. The opening 95 is formed proximally relative to the distal end 94 and is formed in a plane generally orthogonal the fluid flow axis of the fluid delivery lumen 58. In this manner, fluid may be directed out of the side of the fluid delivery lumen and towards the camera 80 coupled to the visualization device 26. In one embodiment, the visualization device 26 is coupled to a fluid delivery nozzle 96, discussed below, in fluid communication with the opening 95 and sized and shaped to facilitate insertion into the distal end 94 of the fluid delivery lumen 58. It should be understood that the distal opening 30 of the tracheal ventilation lumen 14 may be associated with other distal ends of lumens formed in the tubular body 12. For example, the cuff inflation lumen 38 (see FIG. 1) may terminate at distal end 97 and the cable 60 may be inserted into a dedicated lumen that terminates at distal end 98. The cable 60 (e.g., a multi-wire cable) extends from the housing 84 to provide electrical coupling with the camera and light sources. The cable 60 may be routed through a dedicated lumen in the tubular body 12 or may be embedded in or otherwise associated with the tube before terminating in a portion proximal to the tube and a connector 62 (see FIG. 1). In such embodiments, leads or wires from device 26 and the cable 60 may be electrically coupled to the printed wires. In other embodiments, the cable 60 may be connected to a printed circuit board as provided in U.S. patent application Ser. No. 12/981,296, by Sarah Hayman et al., filed Dec. 29, 2010, the disclosure of which is incorporated by reference in its entirety herein for all purposes.

In the depicted embodiment, the fluid delivery nozzle 96 may be inserted via the distal end 94 of the tracheal ventilation lumen 14 of a double-lumen tube. However, it should be understood that nozzle 96 may be used in conjunction with a single lumen tracheal tube. In such an embodiment, the nozzle 96 may be inserted into the fluid delivery lumen 58 via a side wall of the tubular body 12 at a position located distally from a sealing cuff. Further, after application of the visualization device 26 and nozzle 96 to the tubular body 12, the distal shoulder of the cuff (e.g., cuff 34), may be pulled over the visualization device 26 and nozzle 96 to further affix these components to the tubular body 12. In such embodiments, the cuff may be formed from an optically transparent material to avoid distortion of the image through the camera 80.

A distal surface 99 of the visualization device forms a bore, recess, or aperture 100 that accommodates a camera assembly (e.g., a lens and/or other image gathering structures). The aperture 100 may form an annulus or may form a partial annulus (e.g., a U-shape) with an open section 101. The open section 101 may be aligned with opening 95 so that fluid from the fluid delivery lumen 58 is directed towards the camera assembly. For example, during assembly, the housing 84 may be aligned relative to the tubular body 12 such that the open section 101 and the opening 95 are in fluid communication. In other embodiments, for example where the aperture forms a complete annulus, the housing 84 may include an aperture configured to align with the opening 95.

In particular, the orientation of the camera 80 and the housing 84 may be selected so that one or more passageways or openings 95 formed in the fluid delivery lumen 58 may deliver fluid (e.g., water, saline, etc.) directed at the camera lens and/or associated light sources. In such embodiments, the positioning and angle of the opening 95 may be selected to facilitate cleaning of the desired object. In embodiments in which a fluid delivery nozzle 96 is employed, the nozzle 96 is coupled to the fluid delivery lumen 58 to direct the fluid flow towards the appropriate area of the visualization device 26. By providing the nozzle as a separate component, the angle of the fluid flow may be more precisely determined. For example, while a shaped aperture or opening may be difficult to form within the fluid delivery lumen 58 after the tube 10 is cut, the nozzle 96 may be formed separately and from different materials than the tubular body 12, which may be extruded or molded. Further, double-lumen tubes are relatively complex to manufacture. By providing the nozzle 96 and visualization devices 26 as separate components that are attached after formation of the tubular body 12, additional forming steps of the tubular body 12 may be avoided.

The nozzle 96 may be generally sized and shaped for insertion into the fluid delivery lumen. For example, the nozzle may include a barb 102 that is slightly larger than the diameter of the lumen 58. The barb is compressed into the lumen 58 through the distal opening 94, which secures the nozzle within the lumen 58. The body 104 of the nozzle also includes an aperture 106 (e.g., a first opening) that may be aligned with the opening 95. Insertion of the nozzle 96 into the distal end 94 of the fluid delivery lumen 58 may serve to cap the distal end 94. For example, the nozzle 96 may be capped or closed at its distal end 108.

Figure 5:
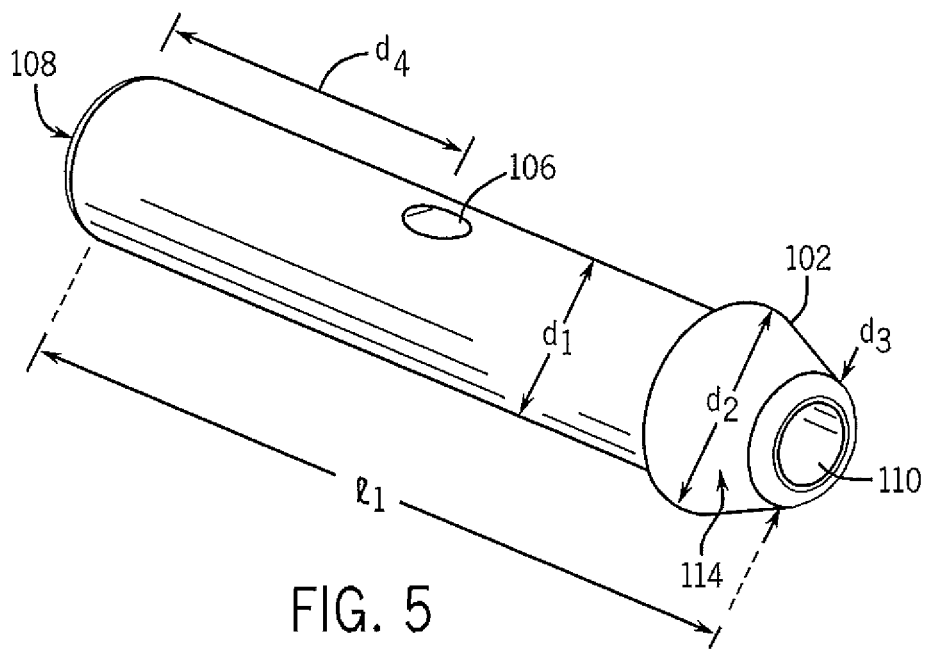
FIG. 5 is perspective view of the fluid nozzle of FIG. 4.

FIG. 5 is a perspective view of the nozzle 96. In particular, the body 104 defines a passageway 110. When the nozzle 96 is inserted into the fluid delivery lumen 58, the passageway 110 is in fluid communication with the lumen 58 to allow fluid to flow into the nozzle 96 and out of the aperture 106. To that end, the diameter $d_1$ of the passageway 110 is about the same diameter or slightly less than the diameter of the fluid delivery lumen 58 through most of the length of the body 104. As noted, part of the barb 102 is larger than the diameter of the lumen 58. For example, the barb may form a taper with a smaller diameter $d_3$ at its proximal end and a larger diameter $d_2$ (e.g., slightly larger than the diameter of the lumen) at its distal end. Generally, the angle of the taper may facilitate insertion into and retention within the fluid delivery lumen. The size and angle of the taper may be selected based on the material properties of the nozzle 96. For example, if the nozzle 96 is formed from a compressible material, the taper may result in a larger diameter $d_3$ than if the nozzle 96 is more rigid. That is, a more rigid material may not permit insertion of a barb 102 that is too large at its largest diameter point. In addition, the length $d_4$ of the nozzle 96 may be selected to align the aperture 106 with the opening 95 formed in the fluid delivery lumen 58 along the exterior surface of the tubular body 12. That is, the distance $d_4$ between the distal end 108 and the aperture 106 may be about the distance between the distal opening 30 of the tracheal ventilation lumen and the opening 95 (see FIG. 4). In particular embodiments, the total length $l_1$ of the nozzle 96 may be about equal to the length of the visualization device along the fluid flow axis of the tube 10.

During assembly, the nozzle 96 may be formed from any suitable material that may be shaped, molded, machined, or otherwise formed into an appropriate configuration. For example, the nozzle 96 may be molded from the same material or materials to form the barb 102 and body 104. In other embodiments, the barb 102 and the body 104 may be formed from materials with different properties. The barb 102 may be formed from a material that is more compressible than the body 104. To that end, the nozzle 96 may be formed and the bard 102 may be overmolded with a suitably compressible material. In another embodiment, certain features of the nozzle 96 may be formed during or after assembly. For example, the aperture 106 may be cut or notched into the body 104 after the nozzle 96 is inserted into the lumen 58. In this manner, the aperture 106 may be more precisely aligned with the opening 95. In one embodiment, the desired location of the aperture 106 is marked when the nozzle 96 is inserted. The nozzle 96 is then removed to form the notch. In other embodiments, the aperture 106 is formed without removing the nozzle 96 from the lumen 58.

Figure 6:
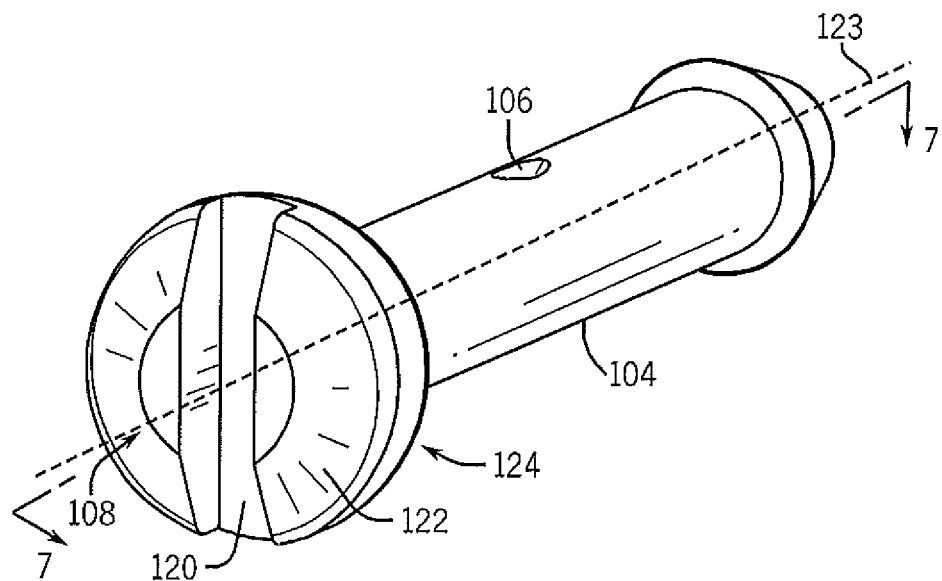
FIG. 6 is perspective view of an alternative fluid nozzle.

FIG. 6 is a perspective view of an alternative nozzle 96 that includes an alignment feature at its distal end 108. In the depicted embodiment, the alignment feature has a groove 120 and a ridge 122 configuration similar to a flathead screw. A suitably-sized tool inserted into the groove 120 may rotate the nozzle 106 about axis 123 to change the position of the aperture 106. In this manner, the aperture 106 may be rotated within the fluid delivery lumen 58 until the aperture 106 is properly aligned. Further, the aperture 106 may feature a colored outline or other alignment features or markings that facilitate proper positioning. In other embodiments, the alignment feature may include a crosshead screw configuration or any surface feature that allows a tool to grip the distal end and rotate the nozzle 106 along the axis 123. The distal end 108 may protrude from the body 104 of the nozzle to create an adhesion surface 124. The adhesion surface 124 may be larger than the fluid delivery lumen 58 and may stop further insertion of the nozzle within the fluid delivery lumen 58, which may help align the aperture 106. Adhesion surface 124 may abut the tubular body 12 and may provide a surface for affixing the nozzle 96 to the tracheal tube 10. Accordingly, an adhesive may be applied to the adhesion surface 124 before the nozzle 96 is inserted into the fluid delivery lumen 58.

Figure 7:
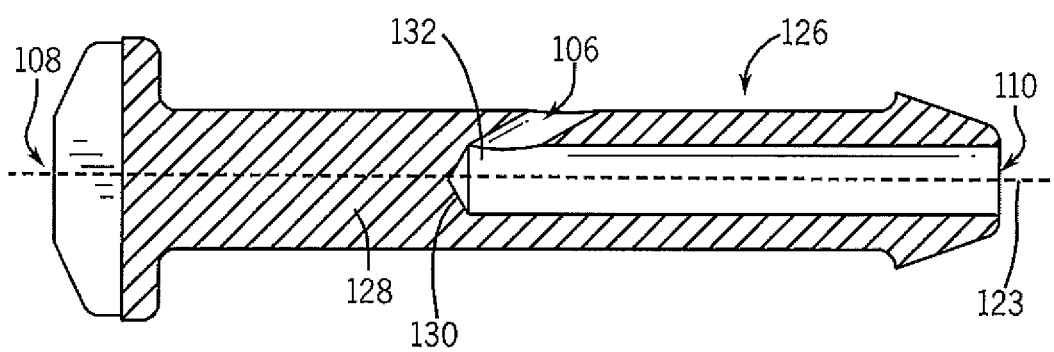
FIG. 7 is a section view of the fluid nozzle of FIG. 6.

As noted, the aperture 106 may provide a shaped or directed flow of fluid to the camera 80. FIG. 7 is a cross-sectional view of the nozzle 96 of FIG. 6. The proximal portion 126 of the nozzle 96 includes the passageway 110, which is configured to be in fluid communication with the fluid delivery lumen 58 when the nozzle 96 is positioned in the lumen 58. The distal portion 128 of the nozzle 96 is closed, i.e., forms a cap that stops fluid flow in a distal direction and instead forces fluid to exit the nozzle 96 through the aperture 106. The nozzle 96 may also include additional fluid-directing features. For example, the distal-most portion 130 of the passageway 110 may be shaped or notched to encourage flow through an angled aperture 106. As fluid flows into the passageway 110, the distal-most portion 130 may not only stop the fluid from advancing, but may facilitate a reversal of fluid flow direction. As shown, the aperture 106 is angled away from the distal end 108 of the nozzle along arrow 132. In certain embodiments, the aperture 106 may be generally orthogonal to the axis 123 of fluid flow along passageway 110 or may be nonorthogonal to the axis 123.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, the embodiments provided herein may be implemented in combination with one another, either all or in part.

What is claimed is:

1. A tracheal tube, comprising:
a first ventilation lumen having a first distal end and a first proximal end;
a second ventilation lumen adjacent to the first lumen, the second ventilation lumen having a second distal end and a second proximal end, and wherein the second ventilation lumen is longer than the first ventilation lumen;
a camera attached to the tracheal tube proximate to the first distal end of the first ventilation lumen;
a fluid delivery lumen coupled to the tracheal tube and configured to deliver a fluid to the camera, wherein the fluid delivery lumen comprises a first opening and a second opening, wherein the first opening is disposed on a side wall of the fluid delivery lumen and is proximal to the-second opening, and wherein the fluid delivery lumen terminate at the second opening; and
a nozzle disposed in the second opening of the fluid delivery lumen to close the fluid delivery distal end, wherein the nozzle comprises a third opening that aligns with the first opening, to form a passageway to deliver the fluid to the camera, and wherein the third opening is angled away from the nozzle distal end in a direction opposite a fluid flow direction in the fluid delivery lumen.

2. The tracheal tube of claim 1, comprising a first cuff disposed around the first ventilation lumen and the second ventilation lumen, and a second cuff disposed around only the second ventilation lumen.

3. The tracheal tube of claim 2, wherein the first distal end is located on the tracheal tube between the first cuff and the second cuff.

4. The tracheal tube of claim 2, wherein the camera is disposed on the first ventilation lumen distally of the first cuff.

5. The tracheal tube of claim 1, wherein the camera is associated with a housing that encircles the first ventilation lumen and the second ventilation lumen.

6. The tracheal tube of claim 1, wherein the fluid delivery lumen is formed in a wall of the first ventilation lumen.

7. The tracheal tube of claim 5, wherein a portion of the housing is embedded within a wall of the first ventilation lumen and the second ventilation lumen.

8. The tracheal tube of claim 5, wherein the housing protrudes less than 5 mm from an exterior surface of the tracheal tube.

9. The tracheal tube of claim 1, wherein the third opening is positioned orthogonal to a fluid flow axis of the fluid delivery lumen.

10. The tracheal tube of claim 1, wherein the second ventilation lumen comprises a positioning feature configured to position the second distal end within a patient's airway.

11. The tracheal tube of claim 10, wherein the positioning feature comprises a protrusion on an exterior surface of the second ventilation lumen, wherein the protrusion is distal to the camera.

12. The tracheal tube of claim 1, wherein the second distal end is curved.

13. The tracheal tube of claim 1, wherein the a field of view of the camera is oriented towards a carina of a patient when the tracheal tube is inserted.

14. The tracheal tube of claim 1, wherein the tracheal tube is configured to be coupled to at least one of a ventilator, a bag for ventilation, inspiration valving, expiration valving, or an air supply.

15. The tracheal tube of claim 1, wherein the second distal end is aligned with an upper bronchus of a patient when inserted.

16. The tracheal tube of claim 1, wherein the tracheal tube comprises a right-stem endobronchial tube.

17. The tracheal tube of claim 1, wherein the second distal end comprises x-ray visible markings.

18. The tracheal tube of claim 1, comprising a cuff inflation lumen that forms a passageway to an exterior of the tracheal tube at a location in fluid communication with an interior of an inflatable cuff.

19. The tracheal tube of claim 1, comprising a divider forming part of and dividing the first ventilation lumen and the second ventilation lumen, wherein the divider extends beyond the first distal end to a portion of an exterior wall of the second ventilation lumen.

20. The tracheal tube of claim 1, wherein the third opening is proximal to the nozzle distal end.

* * * * *